US00PP34168P2

(12) United States Plant Patent
Hogan

(10) Patent No.: US PP34,168 P2
(45) Date of Patent: Apr. 26, 2022

(54) ***HEDERA* PLANT NAMED 'TROPICAL BLIZZARD'**

(50) Latin Name: *Hedera canariensis*
Varietal Denomination: Tropical Blizzard

(71) Applicant: Sean Hogan, Portland, OR (US)

(72) Inventor: Sean Hogan, Portland, OR (US)

( * ) Notice: Subject to any disclaimer, the term of this patent is extended or adjusted under 35 U.S.C. 154(b) by 0 days.

(21) Appl. No.: 17/199,748

(22) Filed: Mar. 12, 2021

(51) Int. Cl.
*A01H 5/00* (2018.01)
*A01H 6/00* (2018.01)

(52) U.S. Cl.
USPC ..... Plt./249
CPC ..... *A01H 6/00* (2018.05)

(58) Field of Classification Search
USPC ..... Plt./249
CPC ..... A01H 5/00; A01H 5/12
See application file for complete search history.

(56) References Cited

PUBLICATIONS https://www.growertalks.com/Newsletters/View/Newsletter/?article=3137; Apr. 7, 2020; 2 pages.*

* cited by examiner

*Primary Examiner* — Kent L Bell
(74) *Attorney, Agent, or Firm* — Weatherly IP Solutions, LLC; Barbara Campbell

(57) ABSTRACT

A new cultivar of *Hedera canariensis* plant named 'Tropical Blizzard' is disclosed and is distinguishable by its naturally prostrate vigorous plant habit which lends itself to training into upright or hanging forms. The leaves of 'Tropical Blizzard' are broad deltate and boldly variegated consisting of mid-dark green patches or mottling appearing to overlay a light yellow to pale green ground. The margins of the leaves of 'Tropical Blizzard' are entire and occasionally narrowly edged grey-purple in color. The stems and petioles of 'Tropical Blizzard' are conspicuously bright red in color when young and red-purple in color when older. 'Tropical Blizzard' is a juvenile form of *Hedera canariensis* on which no flowers or reproductive organs or seed will be present.

2 Drawing Sheets

Genus and species: *Hedera canariensis.*
Variety denomination: 'Tropical Blizzard'.

BACKGROUND

The present disclosure relates to a new and distinct cultivar of *Hedera canariensis,* commonly known as Canary Island Ivy or Algerian Ivy. *Hedera canariensis* is commonly used as a ground cover plant in USDA Hardiness Zone 8 and higher. *Hedera canariensis* is also grown as an indoor or outdoor container plant in many forms including upright growth on a cane or trellis and hanging baskets with trailing stems.

In common with other species of *Hedera, Hedera canariensis* exists as juvenile and adult forms. Juvenile forms of *Hedera* take many years to transform into adult form, and may never do so if repeatedly propagated. Juvenile ivy does not flower and bears palmate lobed leaves arranged alternately along the stem, whereas adult ivy does flower and bears entire ovate leaves arranged spirally along the stem. Juvenile ivy is the predominant form of *Hedera* found in commerce and cultivation. 'Tropical Blizzard' is a juvenile form of *Hedera canariensis* and has not been observed in adult form.

'Tropical Blizzard' was discovered in 2011 by the inventor as a naturally occurring branch sport (a single shoot) with novel mottled variegation which was growing on a plant of *Hedera canariensis variegata* (species, unpatented, unnamed) at the inventor's nursery in Portland, Oreg. The inventor desired to isolate a form of the initial sport which exhibits attractive, uniform and stable variegation. The inventor excised and rooted the shoot mutation and observed the resulting growth for one season. Commencing in 2012, the inventor took selected cuttings from the available stock and repeated the selection and propagation process for four or five cycles. By 2015, the inventor was satisfied that he had isolated a desirable plant for eventual introduction.

The present form of 'Tropical Blizzard' was first asexually propagated in 2015 by the inventor at the inventor's nursery in Portland, Oreg. using the method of stem cuttings. The inventor has confirmed that 'Tropical Blizzard' is stable and reproduces true to type in successive generations of asexual reproduction via stem cuttings.

SUMMARY

The following traits have been repeatedly observed and represent the distinguishing characteristics of 'Tropical Blizzard'. 'Tropical Blizzard' has not been tested under all possible conditions and phenotypic differences may be observed with variations in environmental, climatic, and cultural conditions, without however, any variance in genotype.

1. Unless trained to grow otherwise, 'Tropical Blizzard' exhibits a vigorous prostrate trailing habit.
2. 'Tropical Blizzard' may be grown as a self-supporting small container plant, or trained to grow on canes or trellises or allowed to trail as a hanging basket plant.
3. When hanging or trained upwards, plants of 'Tropical Blizzard' achieve a length or height of approximately 75 cm to 1 m after one season of growth at mean temperature between 15° C. and 25° C.

4. The leaves of 'Tropical Blizzard' are broad deltate, variegated and three-lobed with palmate veination.
5. The variegation of the leaves of 'Tropical Blizzard' consists of mid-dark green patches or mottling appearing to overlay a light yellow to pale green ground.
6. The margins of the leaves of 'Tropical Blizzard' are entire and occasionally narrowly edged grey-purple in color.
7. The stems and petioles of 'Tropical Blizzard' are conspicuous and vary between bright red when young and red-purple in color when older.
8. No flowers or reproductive organs or seed have been observed in growing plants of 'Tropical Blizzard'.

DESCRIPTION OF THE PHOTOGRAPHS

The accompanying color photographs, FIG. 1 and FIG. 2, illustrate the appearance of the new *Hedera* cultivar 'Tropical Blizzard' showing the colors as true as it is reasonably possible to obtain in colored reproductions of this type.

BOTANICAL DESCRIPTION OF THE NEW VARIETY

Figure 1:
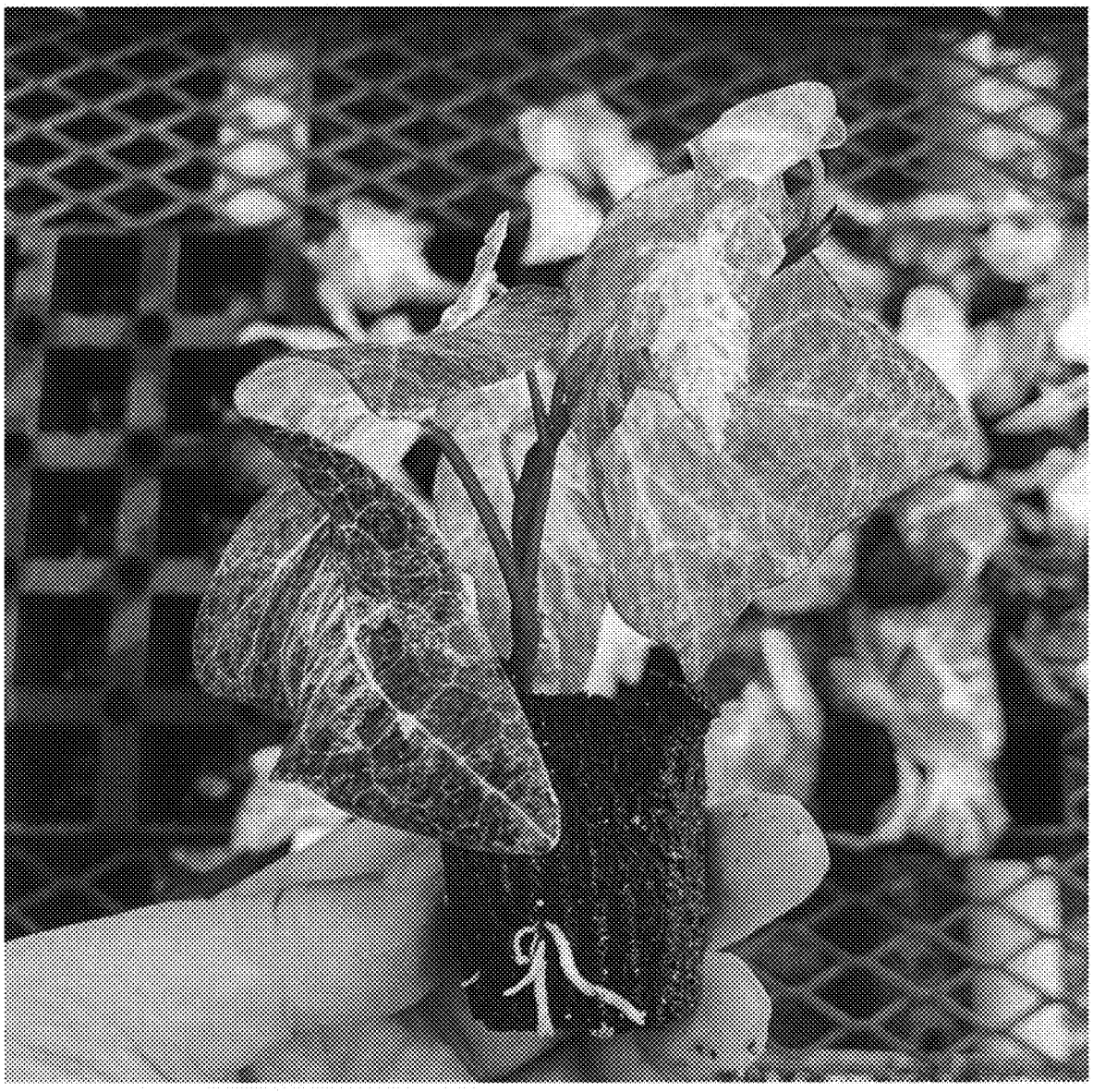
FIG. 1 illustrates a young plant growing in Oxnard, Calif. which is approximately 8-weeks-old after initial rooting and depicts the bright red stems of 'Tropical Blizzard' at this young stage.
Figure 2:
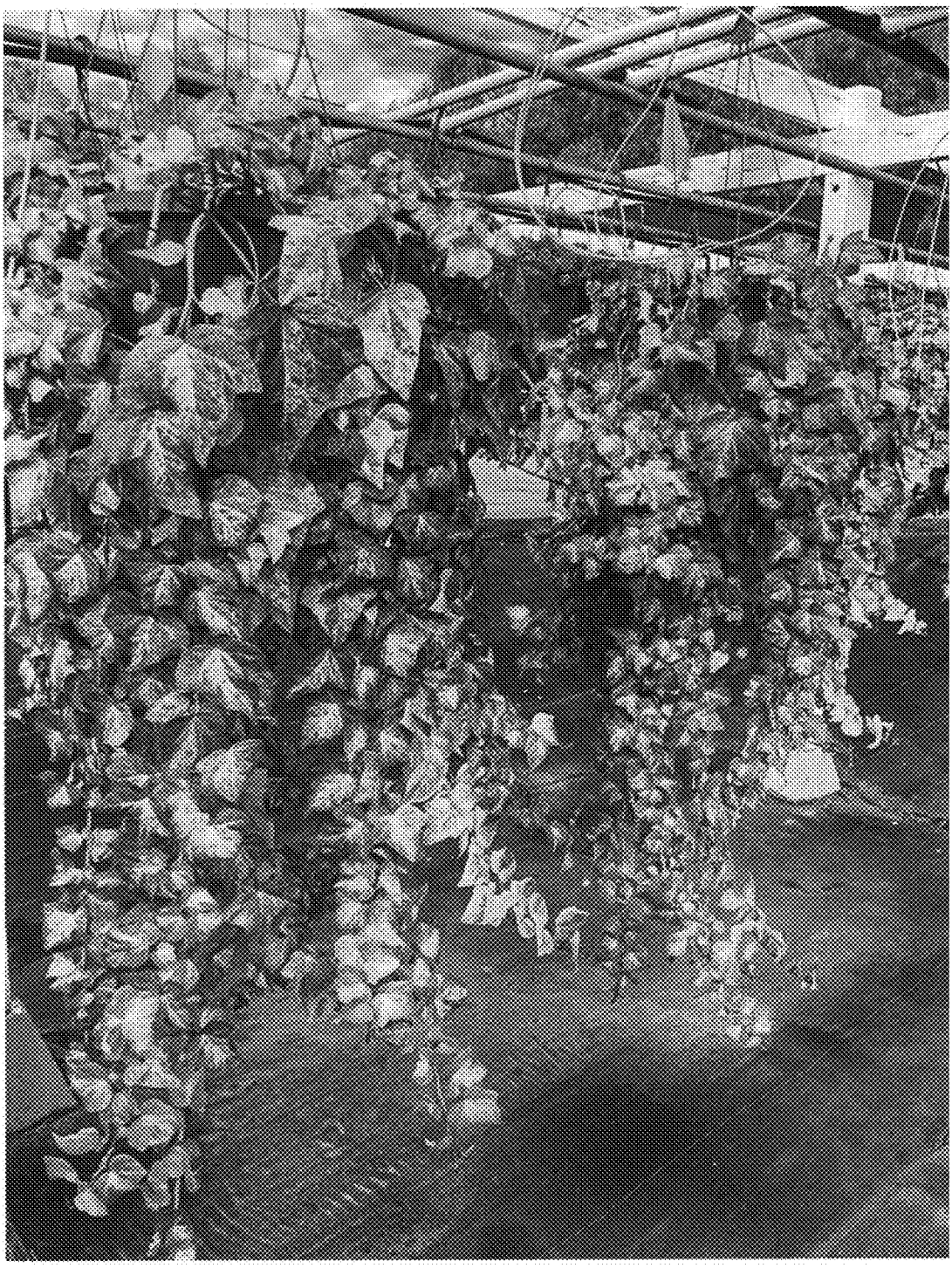
FIG. 2 illustrates one-year-old plants of 'Tropical Blizzard' which have been allowed to trail. The illustrated plants have been grown in a cool greenhouse in San Diego County, Calif. and have not been pruned.

The following is a detailed botanical description of the new variety 'Tropical Blizzard'. Data was collected from trailing plants which had been grown for 12 months from a rooted cutting in a greenhouse in San Diego County, Calif. The color determinations are in accordance with the fifth edition (2007) of The Royal Horticultural Society Colour Chart of The Royal Horticultural Society, London, England, except where general color terms of ordinary dictionary significance are used. The plants were grown entirely naturally without pruning or the use of growth-regulating chemicals.

Classification:

*Family.*—Araliaceae.

*Genus.*—*Hedera.*

*Species.*—*canariensis.*

*Common name.*—Canary Island Ivy, Algerian Ivy.

Parentage: Naturally occurring branch shoot mutation found on parent plant *Hedera canariensis variegata* (species, unnamed).

Plant:

*Form.*—Juvenile form of the species in which flowers are not formed.

*Vigor.*—Vigorous trailing habit with strong apical dominance.

*Propagation method.*—Stem cuttings retaining at least one node.

*Roots.*—Fleshy, up to 1.5 mm in diameter, color initially white NN155D becoming grey-yellow 162D.

*Time to develop roots.*—4 to 5 weeks are required at air and soil temperate around 20° C. for a newly planted cutting to become established on its own roots.

*Crop time.*—For quart container, 10 to 12 weeks from planting a rooted young plant. Larger containers including plants for training vertically or hanging may take upwards of 3 months to finish, depending on desired final height or length.

*Uses.*—Ornamental indoor or outdoor in containers, or trained as a vining plant, or planted and trailing in hanging baskets. Ground cover and mass landscaping in frost-free climates.

*Type.*—Vining perennial in USDA Zone 8 and warmer.

*Overall dimensions.*—When hanging or trained upwards, plants of 'Tropical Blizzard' achieve a length or height of approximately 75 cm to 1 m after one season of growth at a mean temperature between 15° C. and 25° C. and has a diameter of approximately 25 cm to 40 cm.

*Cultural requirements.*—Grow in sun or part shade with moderate water and well-draining soil except that prolonged exposure to full summer sun may bleach or scorch the juvenile foliage.

*Hardiness.*—USDA Zone 8.

*Growth habit.*—Naturally prostrate unless trained.

*Basal branching.*—Vigorous basal branching. Basal branches exhibit strong apical dominance.

*Lateral branches.*—Absent on most main stems. Present if stimulated by pruning.

Stems:

*Stem quantity.*—5 to 8 stems per plant.

*Stem dimensions* (*observed plants*).—150 cm in length, up to 3 mm in diameter.

*Internode distance.*—Ranges from 5 mm towards apex to 6 cm towards base.

*Stem color.*—Ranges between 45B (young stems) to 181A to 181C (older stems).

*Stem shape.*—Cylindrical.

*Stem texture.*—Glabrous.

*Stem strength.*—Strong and wiry.

Leaves:

*Type, arrangement.*—Simple, alternate.

*Attachment.*—Petiolate.

*Quantity per stem.*—40 to 50.

*Shape.*—Broad deltate overall, palmate, 3-lobed.

*Dimensions* (*leaf fully developed and expanded*).—12 cm. in length, 13.5 cm in width across opposite lobes.

*Texture, surface.*—Thick and leathery, glaucous (both surfaces).

*Venation.*—Palmate.

*Vein color* (*both surfaces*).—154C.

*Color* (*adaxial surface*).—Broad patches or large mottling bright mid-dark green 141A to 141B in color, appearing to overlay ground color of very light green to pale yellow-green 154D to 3D.

*Color* (*abaxial surface*).—Irregular interveinal patches of dull green and brown, ranging between 144B and 152B.

*Margin.*—Entire, young foliage narrowly edged 185B.

*Apex* (*each lobe*).—Acute.

*Base.*—Cordate.

Petiole:

*Shape.*—Round.

*Length.*—Youngest leaves, 5 mm; oldest leaves at base up to 12 cm.

*Diameter.*—1.5 mm to 2.5 mm.

*Texture.*—Glabrous.

*Color.*—Ranges between 45B (young leaves) to 181A to 181C (mature leaves).

Inflorescence, reproductive organs, seed: Absent.

Disease and pest resistance or susceptibility: None observed.

COMPARISON WITH PARENTAL LINE

Whereas the parent *Hedera canariensis variegata* exhibits unstable variegated foliage, the foliage of 'Tropical Blizzard' is uniform and consists of larger leaves which exhibit brighter mid-green variegation. In addition, the foliage of 'Tropical Blizzard' is more tightly spaced along the stem which results in a more-dense plant habit and appearance. 'Tropical Blizzard' has been observed to take on a rose-colored glow, ranging between 51B and 51D, in cooler high light conditions.

COMPARISON WITH KNOWN VARIETY

The closest known named variegated variety of *Hedera canariensis* known to the inventor is *Hedera canariensis* 'Gloire de Marengo' (unpatented). 'Gloire de Marengo is used as an ornamental indoor and outdoor plant grown on canes or trellises. The leaves of 'Gloire de Marengo' consist of muted patches of pale and mid grey-green and bear wide cream margins. 'Tropical Blizzard' bears bold mid-dark green foliage without prominent margins.

I claim:

1. A new and distinct cultivar of *Hedera* plant named 'Tropical Blizzard' as described and illustrated herein.

* * * * *